United States Patent
Kim et al.

(10) Patent No.: US 9,629,372 B2
(45) Date of Patent: Apr. 25, 2017

(54) SELECTIVE TERMITE REPELLENT COMPOSITION USING NATURAL PLANT-BASED MATERIALS

(71) Applicant: CLEAN BIO CO., LTD., Daejeon (KR)

(72) Inventors: Hae-Joong Kim, Daejeon (KR); Seung-Hee Jang, Gyeonggi-do (KR)

(73) Assignee: CLEAN BIO CO., LTD., Daejeon (KR)

( * ) Notice: Subject to any disclaimer, the term of this patent is extended or adjusted under 35 U.S.C. 154(b) by 131 days.

(21) Appl. No.: 14/398,805

(22) PCT Filed: Nov. 22, 2012

(86) PCT No.: PCT/KR2012/009894
§ 371 (c)(1),
(2) Date: Nov. 4, 2014

(87) PCT Pub. No.: WO2014/073730
PCT Pub. Date: May 15, 2014

(65) Prior Publication Data
US 2015/0272134 A1    Oct. 1, 2015

(30) Foreign Application Priority Data
Nov. 9, 2012   (KR) .................. 10-2012-0126505

(51) Int. Cl.
*A61K 36/00* (2006.01)
*A01N 65/44* (2009.01)
*A01N 65/00* (2009.01)
*A01M 29/12* (2011.01)

(52) U.S. Cl.
CPC ............. *A01N 65/44* (2013.01); *A01M 29/12* (2013.01); *A01N 65/00* (2013.01)

(58) Field of Classification Search
None
See application file for complete search history.

(56) References Cited

U.S. PATENT DOCUMENTS

| 7,387,805 B2 | 6/2008 | Tsuzaki |
| 2010/0136102 A1 | 6/2010 | Franklin et al. |
| 2011/0124502 A1 | 5/2011 | Enan |

FOREIGN PATENT DOCUMENTS

| JP | 63-30402 A | 2/1988 |
| JP | 10-46061 | 2/1998 |
| JP | 2002-60304 A | 2/2002 |
| JP | 2002-60308 A | 2/2002 |
| JP | 2010138117 A * | 6/2010 |
| JP | 2011-93809 | 5/2011 |
| JP | 5455556 | 3/2014 |
| KR | 2002070598 A * | 9/2002 |
| KR | 10-2005-0013326 | 2/2005 |
| KR | 10-2008-0093022 | 10/2008 |
| WO | WO 2005/003112 | 1/2005 |
| WO | WO 2011/002929 | 1/2011 |

OTHER PUBLICATIONS

International Search Report for PCT/KR2012/009894, mailed May 15, 2013.
Notification of Reasons for Refusal, JP Patent Application Mo. 2014-545804 ("Selective Termite Repellent Composition Using Natural Plant-Based Materials" Nov. 22, 2012), Applicant Kurata, Feb. 5, 2015.
Notification of Reasons for Refusal, JP Patent Application Mo. 2014-545804 ("Selective Termite Repellent Composition Using Natural Plant-Based Materials" Nov. 22, 2012), Applicant Kurata, Oct. 23, 2015.

* cited by examiner

*Primary Examiner* — Qiuwen Mi
(74) *Attorney, Agent, or Firm* — Nixon & Vanderhye P.C.

(57) ABSTRACT

The present invention relates to a termite repellent composition, and more specifically, to a selective termite repellent composition, which does not cause side effects such as environmental pollution by using plant-based materials, and which eliminates termites but not other ants. To this end, the selective termite repellent composition according to the present invention simultaneously comprises citronella oil, lemongrass oil, and a ginko leaf extract.

3 Claims, 2 Drawing Sheets

1) 0 day (before treatment with composition)

| Example 1-1 | Control |

2) 0 day (after 6 hours)

| Example 1-1 | Control |

3) after 1 day

| Example 1-1 | Control |

4) after 2 days 5) after 5 days 6) after 7 days

SELECTIVE TERMITE REPELLENT COMPOSITION USING NATURAL PLANT-BASED MATERIALS

This application is a National Phase of International Application No. PCT/KR2012/009894, filed on Nov. 22, 2012, which designated the U.S. and claims priority to KR Application No. 10-2012-0126505, filed on Nov. 9, 2012, the entire contents of each of which are hereby incorporated herein by reference.

TECHNICAL FIELD

The present invention relates to a composition for repelling termites (white ants), and more particularly, to a selective termite repellent composition, which comprises natural substances of plant origin that do not cause adverse effects such as environmental pollution and which eliminates only termites but not other ants.

Due to the destruction of ecosystems and environmental changes, damage to wooden structures by termites is increasing suddenly, and damage to cultural assets by termites is also occurring continuously. Thus, the present invention is intended to provide an optimal termite repellent that is formulated by a novel method using natural plant extracts that repel termites, and has a novel composition. The termite repellent according to the present invention is a formulation prepared so as to maximize the fragrance of natural oils.

BACKGROUND ART

The present invention relates to a repellent composition for controlling termites, which are sprayed onto wooden structures or the like for the purpose of preventing damage to wood from being caused by termites.

Termites are insects belonging to the order Isoptera, and recently, the order Isoptera has been classified as a suborder of the order Dictyoptera. Unlike their name suggests, termites are insects that are more closely allied to cockroaches than to ants of the order Hymenoptera.

It is known that only two species of termites which are termites (*Reticulitermes speratus kyushuensis* Morimoto) and house termites (*Coptotermes formosanus* Shiraki) are found in Korea. Termites that are found in Korea are also named Japanese termites and are widely distributed throughout Korea. However, house termites are very rarely found in areas near the southern coast of Korea, including Busan and Jinju.

Termites are insects that cause serious damage to old wooden structures and wooden cultural assets. Termites penetrate or eat into wood, and thus it can be observed that wood damaged by termites has a space inside it. If the major portion of a wooden structure, which supports a load, is damaged by termites, unexpected events such as the collapse of the structure will occur.

In the prior art, in order to prevent the above-described damage to wooden structures from occurring, chemical insect repellents or insecticides were sprayed onto the wooden structures. However, because liquid agents that are mainly used in such repellents and insecticides are chemically synthesized compounds and contain large amounts of toxic synthetic organic solvents, the organic solvents evaporate during the spraying or application of the agents, and the volatile organic solvents come into contact with the skin or are inhaled into the body through the respiratory organ to cause chemical toxicity. In addition, the volatile organic solvents cause environmental pollution. In other words, the above-described methods have many problems, including the occurrence of resistance, secondary toxicity, and environmental pollution such as long-term residence, and disadvantages such as short-term effects.

Moreover, some natural termite repellents have a disadvantage in that they eliminate even queen ants required for the propagation of termites, and thus repel even worker ants known as natural enemies of termites, thereby suppressing a decrease in termites in the ecosystem. In order to overcome this problem, the development of natural substance-based repellents harmless to non-target animals has recently received increasing attention.

Korean Patent Publication No. 10-544605 (entitled "Arylpyrrole for protecting wood, wooden articles and wooden structures from attack of insects") discloses a technology of blocking the access of wood-attacking insects (wood-eating insects such as termites, army ants and wood-destroying beetles) by presenting chemical stimuli to the insects. It discloses protecting wood from the attack of wood-eating insects by treating wood, wooden articles, wooden structures or soil around them with an arylpyrrole compound. It suggests that the compound is very effective for protecting wood, wooden articles and wooden structures from damage and destruction that are caused by particularly termites. However, the compound provides a toxin that is also effective against other insects, and thus can induce toxicity in undesired targets.

Korean Patent Publication No. 10-634082 (entitled "Termite control device") discloses a termite control device for controlling termites that adversely affect the lifespan of wooden cultural assets or various wooden structures. This device adopts a physical heating method employing electric current and frequency and is based on the properties of termites that are weak against heat. However, this device causes a problem in terms of appearance, because it is disposed on facilities. In addition, it has disadvantages in that termites are introduced again when the device is removed, and in that power should be continuously supplied thereto.

In conclusion, the above-described patents do not disclose the effective and safe repelling of termites. In addition, the effective use of plant-based essence oil as an selective termite repellent has not yet been reported.

DISCLOSURE

Technical Problem

The present invention has been made in order to overcome the disadvantages of conventional termite repellents as described above, and it is an object of the present invention to provide a composition for selectively repelling termites, which can substitute for conventional insecticides comprising toxic chemical materials, is environmentally friendly, and can eliminate only termites without eliminating other ants.

Another object of the present invention is to formulate natural components in combination so as to significantly increase the synergistic effects of the components to thereby maximize the repelling effect of the components.

Technical Solution

In order to accomplish the above objects, the present invention provides a composition for selectively repelling termites, which comprises a combination of citronella oil, lemongrass oil and a ginkgo leaf extract.

Herein, the ginkgo leaf extract may be extracted by ethanol.

More specifically, the composition for selectively repelling termites according to the present invention may comprise 0.1-20 wt % of citronella oil, 0.1-20 wt % of lemongrass oil, 0.01-1 wt % of the ginkgo leaf extract (as powder), and 60-99 wt % of ethanol.

More preferably, the contents of citronella oil and lemongrass oil in the composition are 3-10 wt %, respectively.

It is to be understood that the composition of the present invention may further comprise other components that do not impair the functions of the above-described components. For example, the content of ethanol in the composition may be reduced, and other components may be added to the composition.

Citronella oil that is used as one of the main components of the composition according to the present invention contains, as active ingredients, geraniol, camphene, limonene, citronellal and the like, and has lemon fragrance. It blocks the access of insects and mosquitoes, and thus has been used as a natural insect repellent. Also, it was classified as a non-toxic substance by the US EPA, is harmless to the human body, and can be used even for children.

The citronella oil is used in an amount of 0.1-20 wt %, and preferably 3-10 wt %, based on the total weight of the composition. If the citronella oil is used in an amount of less than 0.1 wt % based on the total weight of the composition, the termite repellent effect cannot be exhibited, and if it is used in an amount of more than 10 wt %, it will be difficult to handle, due to its strong fragrance.

Lemongrass oil that is used as one of the main components of the composition according to the present invention contains, as active ingredients, geranial, neral and the like, and has refreshing grass fragrance and lemon fragrance. It can prevent decomposition from being caused by bacteria and fungi, because it contains flavor components that are hated by flies, ticks, mosquitoes and the like, and has strong disinfectant activity and healing activity.

The lemongrass oil is used in an amount of 0.1-20 wt %, and preferably 3-10 wt %, based on the total weight of the composition. If the lemongrass oil is used in an amount of less than 0.1 wt % based on the total weight of the composition, the termite repellent effect cannot be exhibited, and if it is used in an amount of more than 10 wt %, it will be difficult to handle, due to its strong fragrance.

The gingko leaf extract that is used as one of the main components of the compositions according to the present invention is prepared by extracting gingko leaves with ethanol. This extract contains butyric acid and the like as active ingredients, and thus can block the access of noxious insects such as cockroaches and exhibit insecticidal and disinfectant activities.

The gingko leaf extract is used in an amount of 0.01-1 wt % based on the total weight of the composition. It is used in an amount of more than 1 wt % based on the total weight of the composition, it will be difficult to handle, due to its strong fragrance.

Ethanol that is used in the present invention is a solvent that enables the active ingredients (citronella oil, lemongrass oil and the ginkgo leaf extract) to be easily mixed, and can evaporate after deposition of the active ingredients during the use of the composition.

Advantageous Effects

The composition for repelling termites according to the present invention comprises natural substances. It may be applied to old wooden structures, wooden cultural assets or the like for the purpose of preventing damage to wood from being caused by termites, thereby exhibiting the effect of repelling termites without causing other adverse effects, and has control effect against worker ants that are natural enemies of termites.

MODE FOR INVENTION

Figure 1A:
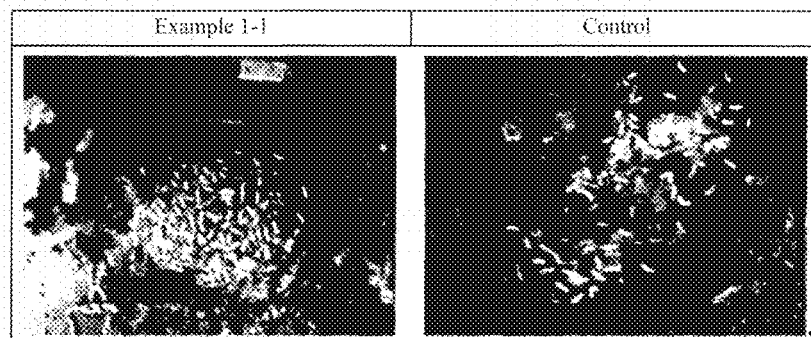
FIGS. 1a and 1b are comparison photographs showing the results of spraying a termite-repelling composition of Example 1-1 into half of a cage and allowing the half to stand for 1 week while allowing the remaining half to stand without spraying the composition thereto in order to examine whether the composition repels termites.
Figure 1A:
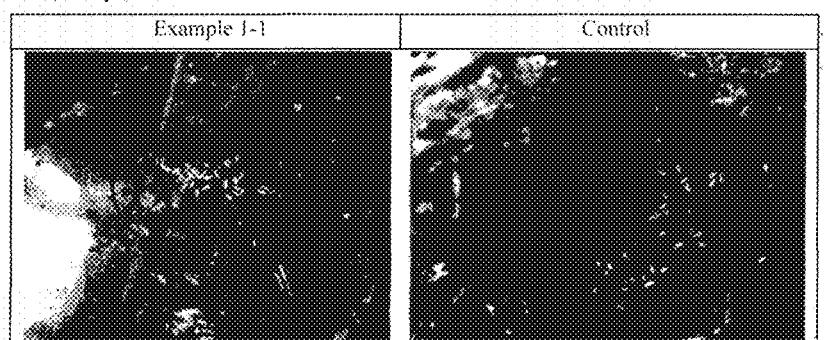
Figure 1A:
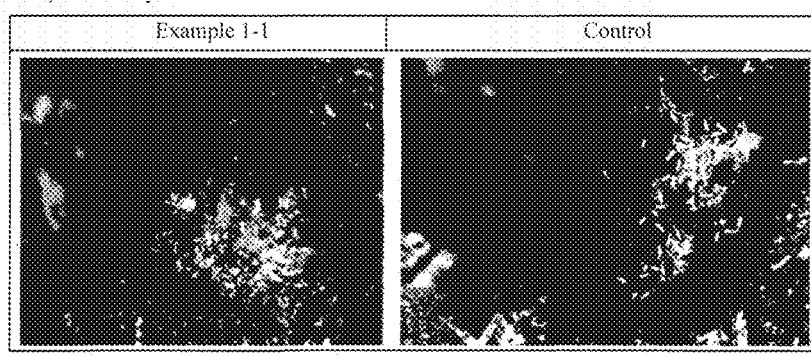

Hereinafter, the present invention will be described in further detail with reference to examples. However, the scope of the present invention is not limited by these examples.

Example 1: Preparation of Termite-Repelling Compositions

Citronella oil (model: HP-95666, manufactured by Hanbit Flavor & Fragrance Co., Ltd.), lemongrass oil (model: HP-95667, manufactured by Hanbit Flavor & Fragrance Co., Ltd.) and a gingko leaf extract powder (obtained by drying gingko leaves, extracting the dry leaves with 70% ethanol at a weight ratio of 1:20 at 94 for 4.5 hours, and filtering and concentrating the extract) were mixed uniformly in a mixer, and then ethanol was added thereto, followed by stirring.

The contents of components in a composition of Example 1-1 were 5 wt % for lemongrass oil, 6 wt % for citronella oil, 0.05 wt % for a gingko leaf extract (as powder), and 88.95 wt % for ethanol. Compositions of other Examples were prepared to have the contents shown in Table 1 below.

TABLE 1

| Components (wt %) | Example 1-1 | Example 1-2 | Example 1-3 | Example 1-4 |
| --- | --- | --- | --- | --- |
| Lemongrass oil | 5 | 5 | 0 | 5 |
| Citronella oil | 6 | 6 | 6 | 0 |
| Gingko leaf extract | 0.05 | 0 | 0.05 | 0.05 |
| Ethanol | 88.95 | 89 | 93.95 | 94.95 |

Experimental Example 1: Termite-Repelling Effects of Termite-Repelling Compositions In order to evaluate the termite-repelling effects of the termite-repelling compositions prepared in the above Examples, a termite colony was purchased from Biobiba Ant Kingdom (Korea), and the termite-repelling effects of the compositions were examined at the laboratory scale using the termite colony.

Under laboratory conditions, trees for inhabitation of termites were placed in both halves of each cage, divided by the middle portion, after which an acclimation period of 1 week was provided.

Each of the termite-repelling compositions was sprayed into half of each cage, but was not sprayed into the remaining half, and then the cages were allowed to stand. The number of termites in the cage sprayed with each composition was counted for 1 week, and the results of the measurement are shown in Table 2 below.

As can be seen in Table 2, among the cage half portions to which the termite-repelling compositions were applied, the cage half portion, to which the composition of Example 1-1 containing all lemongrass oil, citronella oil and the gingko leaf extract was applied, showed complete disappearance of termite inhabitation. In the cases of the compositions of Examples 1-2, 1-3 and 1-4, the number of termites was reduced, but termites did not completely disappear. Although not shown in Table 2, it could be observed that, in all the four cases, the number of termites in the remaining half portion, to which each composition was applied, increased.

TABLE 2

|  | Example 1-1 | Example 1-2 | Example 1-3 | Example 1-4 |
|---|---|---|---|---|
| Before treatment with composition | 70 | 80 | 80 | 70 |
| 6 hours | 30 | 60 | 80 | 70 |
| 1 day | 20 | 50 | 60 | 60 |
| 2 days | 10 | 50 | 50 | 60 |
| 5 days | 0 | 30 | 40 | 50 |
| 7 days | 0 | 20 | 40 | 50 |

* The number of termites was counted in 10, because accurate counting by the activity of termites was impossible.

Figure 1B:
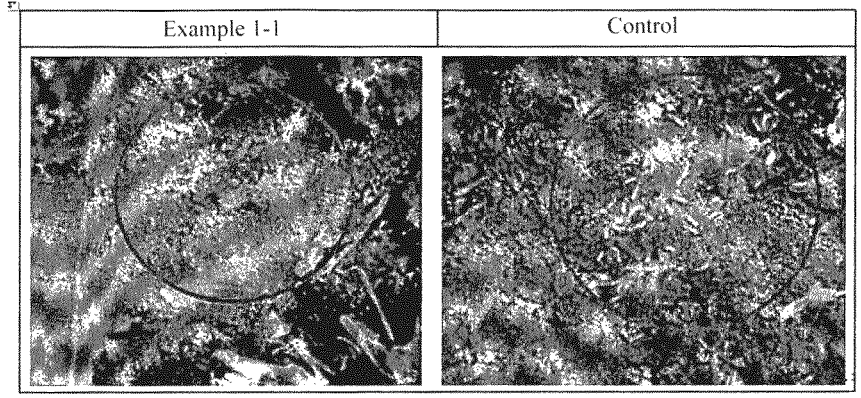
Figure 1B:
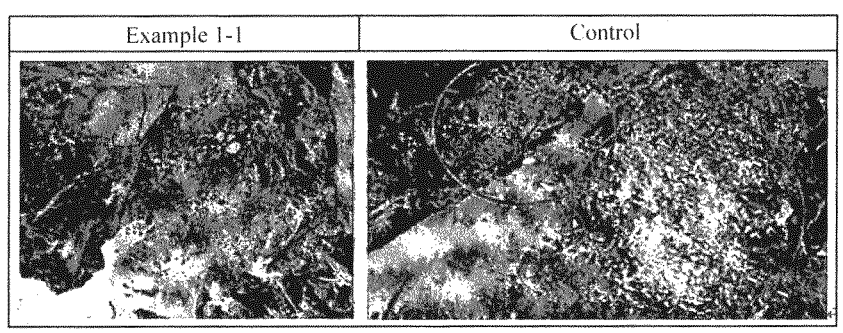
Figure 1B:
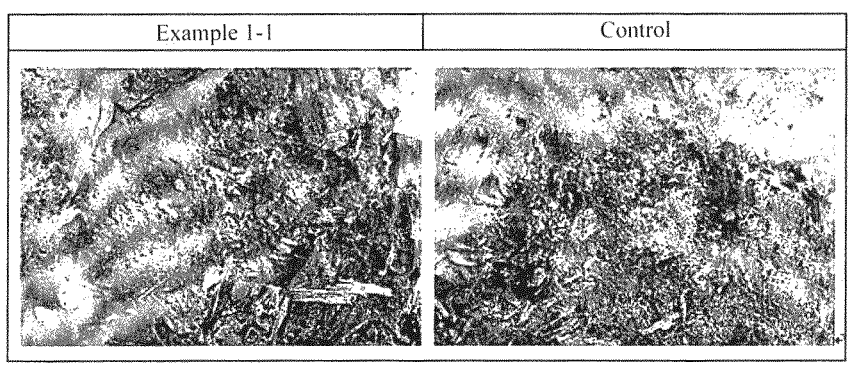

FIGS. 1a and 1b are photographs showing the results of spraying a termite-repelling composition of Example 1-1 into half of a cage and allowing the half to stand for 1 week while allowing the remaining half to stand without spraying the composition thereto in order to examine whether the composition repels termites. As can be seen therein, termites in the applied half portion completely disappeared at 5 days of observation, like the results shown in Table 2. At 7 days, it was observed that termites in the remaining half portion, to which the termite-repelling composition was not applied, were all dead, suggesting that the composition exhibits an insecticidal effect against termites in a closed space.

Table 3 below shows the results of counting the number of termites for 7 days after spraying each of the compositions onto wooden structures that were damaged by termites and had termites therein. As can be seen in Table 3, the composition of Example 1-1 had a better effect.

TABLE 3

|  | Example 1-1 | Example 1-2 | Example 1-3 | Example 1-4 |
|---|---|---|---|---|
| Before treatment with composition | 270 | 290 | 320 | 330 |
| 1 day | 120 | 220 | 210 | 200 |
| 2 days | 20 | 180 | 110 | 90 |
| 5 days | 0 | 90 | 40 | 30 |
| 7 days | 0 | 50 | 0 | 0 |

* The number of termites was counted in 10, because accurate counting by the activity of termites was impossible.

Experimental Example 2: Evaluation of Whether Termite-Repelling Composition Repels Worker Ants In order to evaluate whether the termite-repelling composition prepared in the above Example repels worker ants, a worker ant colony was purchased from Biobiba Ant Kingdom (Korea), and the worker ant-repelling effect of the composition was examined at the laboratory scale using the worker ant colony.

In order to examine the worker ant-repelling effect of the composition prepared in Example 1-1, a sand layer having a thickness of 5 cm was prepared, after which an acclimation period of 1 week was provided. After worker ants have secured their habitat, feed was placed 15 cm apart from the habitat and was treated with each composition, and the accession of worker ants thereto was examined.

Table 4 below shows the change in number of worker ants by the termite-repelling composition of the present invention.

As can be seen in Table 4, the accession of worker ants to the feed was limited for 2 days after treatment with the composition, but was observed after 2 days, suggesting that the composition does not repel worker ants.

TABLE 4

|  | 0 day | 1 day | 2 days | 3 days | 4 days | 5 days |
|---|---|---|---|---|---|---|
| Number of worker ants | 35 | 0 | 0 | 13 | 36 | 41 |

* The number of worker ants which access to feed was counted.

The invention claimed is:

1. A composition for selectively repelling termites to prevent damage to wood, the composition comprising 0.1-20 wt % of citronella oil, 0.1-20 wt % of lemongrass oil, 0.01-1 wt % of a ginkgo leaf extract and 60-99 wt % of ethanol.

2. The composition of claim 1, wherein the ginkgo leaf extract is extracted by ethanol.

3. The composition of claim 1, wherein the contents of citronella oil and lemongrass oil are 3-10 wt %, respectively.

* * * * *